United States Patent
Reddy

(10) Patent No.: US 9,598,346 B2
(45) Date of Patent: Mar. 21, 2017

(54) ENANTIOSELECTIVE PROCESS FOR THE PREPARATION OF ENANTIOMERS OF SEX PHEROMONES

(71) Applicant: COUNCIL OF SCIENTIFIC AND INDUSTRIAL RESEARCH, New Delhi (IN)

(72) Inventor: Dumbala Srinivasa Reddy, Pune (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 14/763,449

(22) PCT Filed: Jan. 24, 2014

(86) PCT No.: PCT/IN2014/000057
§ 371 (c)(1),
(2) Date: Jul. 24, 2015

(87) PCT Pub. No.: WO2014/115172
PCT Pub. Date: Jul. 31, 2014

(65) Prior Publication Data
US 2015/0361025 A1    Dec. 17, 2015

(30) Foreign Application Priority Data
Jan. 24, 2013   (IN) .......................... 0195/DEL/2013

(51) Int. Cl.
| C07C 29/143 | (2006.01) |
|---|---|
| C07C 29/147 | (2006.01) |
| C07C 29/92 | (2006.01) |
| C07C 41/30 | (2006.01) |
| C07C 67/00 | (2006.01) |
| C07C 67/08 | (2006.01) |
| C07C 67/293 | (2006.01) |
| C07D 275/06 | (2006.01) |

(52) U.S. Cl.
CPC .......... *C07C 67/293* (2013.01); *C07C 29/143* (2013.01); *C07C 29/147* (2013.01); *C07C 29/92* (2013.01); *C07C 41/30* (2013.01); *C07C 67/00* (2013.01); *C07C 67/08* (2013.01); *C07D 275/06* (2013.01); *C07B 2200/07* (2013.01); *C07B 2200/09* (2013.01); *C07C 2101/10* (2013.01)

(58) Field of Classification Search
CPC ..... C07C 29/143; C07C 29/147; C07C 29/92; C07C 41/30; C07C 67/00; C07C 67/08; C07C 67/293; C07C 2101/10; C07D 275/06; C07B 2200/07; C07B 2200/09
See application file for complete search history.

(56) References Cited

PUBLICATIONS

Zou and Millar, "Improved Synthesis of the Pheromone of the Longtailed Mealybug", Synlett 2010, No. 15, 2319-2321.
Zou and Millar, "Synthesis of the Pheromone of the Longtailed Mealybug, a Sterically Congested, Irregular Monoterpenoid", J. Org. Chem. 2009, 74, 7207-7209.

*Primary Examiner* — Paul A Zucker
*Assistant Examiner* — Mark Luderer
(74) *Attorney, Agent, or Firm* — DLA Piper LLP (US)

(57) ABSTRACT

The invention disclosed herein relates to an enantioselective process for preparation of biologically active (R) and (S) enantiomers of sex pheromones of the long-tailed Mealybug with high enantiopurity having significant biological activity. Further, the invention provides absolute configuration of synthesized R and S enantiomers.(I)

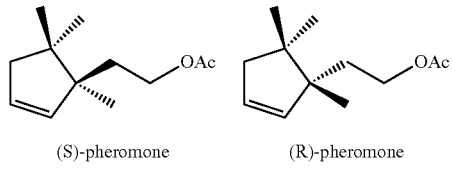

(S)-pheromone         (R)-pheromone

12 Claims, 1 Drawing Sheet

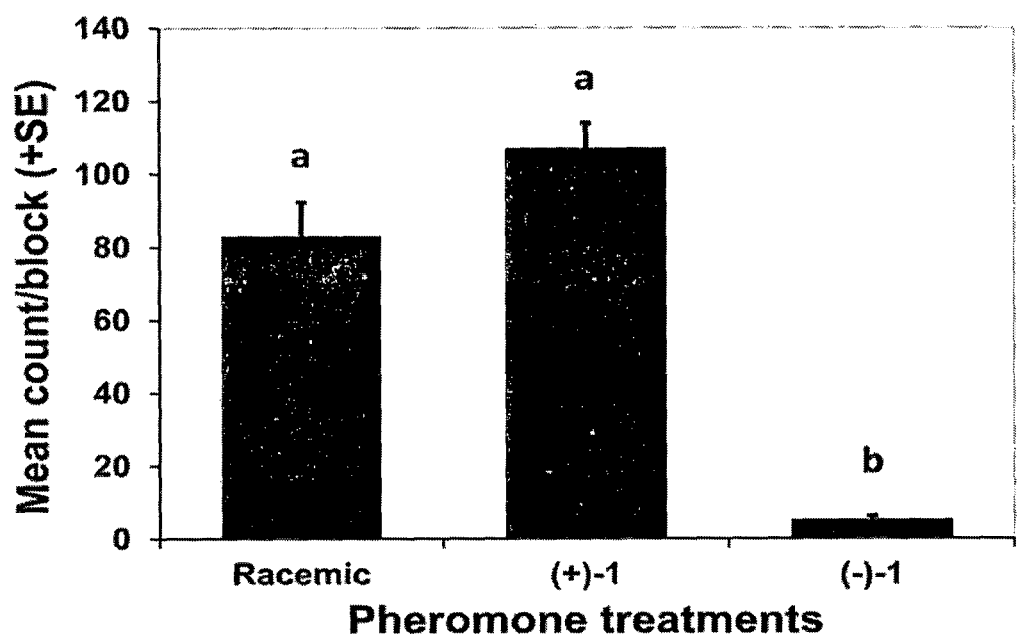

ENANTIOSELECTIVE PROCESS FOR THE PREPARATION OF ENANTIOMERS OF SEX PHEROMONES

CROSS-REFERENCE TO RELATED APPLICATIONS

This application is a 35 USC §371 National Stage application of International Application No. PCT/IN2014/000057 filed Jan. 24, 2014, now pending; which claims the benefit under 35 USC §119(a) to India Application Serial No. 0195/DEL/2013 filed Jan. 24, 2013. The disclosure of each of the prior applications is considered part of and is incorporated by reference in the disclosure of this application.

FIELD OF THE INVENTION

The present invention relates to an enantioselective process for the preparation of enantiomers of sex pheromones of the long-tailed Mealybug with high enantiopurity having significant biological activity.

Further, the invention provides absolute configuration determination of synthesized enantiomers of sex pheromones of the long-tailed Mealybug.

BACKGROUND OF THE INVENTION

Pheromones are chemicals released by an organism into its environment enabling it to communicate with other members of its own species.

Mealy bugs are known to spoil crops such as grapes, pears etc., especially the long tailed mealy bug. The long-tailed Mealybug is scientifically known as *Pseudococcus longispinus* (Targioni-Tozzetti).

The racemic form of the pheromone was synthesized synthetically by the Miller group after identifying the structure of isolated pheromone. Miller has published that 25 µg is sufficient to attract mealy bug for three months. When sprayed on crops, the male bugs are attracted and then they are killed. Male population is thus decreased.

Pheromones play an important role in chemical communication among organisms. Various chiral and non-racemic pheromones have been identified since the late 1960s. Their enantioselective syntheses were achieved so as to establish the absolute configuration of the naturally occurring pheromones and also to clarify the relationship between absolute configuration and the bioactivity of the chiral pheromones.

Synthesis of pheromones is an important and arising field of research to establish the structures and also to provide sufficient material to carry out biological studies. In general, natural pheromones are available in very limited quantities (usually in µg by killing several bugs) which restrict the extensive field trials. To overcome such constrain several methods have been reported in the literature to construct low molecular weight pheromones.

Accordingly Mori K et al. in *Current Organic Synthesis*, 2004, Vol. 1, No. 1 disclosed various aspects of pheromone synthesis where methodologies such as organoborane reactions, organotransition metal chemistry including olefin metathesis, asymmetric epoxidation, asymmetric dihydroxylation, other asymmetric chemical processes was demonstrated.

Recently, pioneering work from Miller's group led to the identification and synthesis of several interesting pheromones from mealybugs; particularly the article disclosed in Journal of Chemical Ecology, Vol. 31, No. 12, December 2005 discloses first example of monoterpenoid structural motif sex pheromone of the obscure mealybug, *Pseudococcus viburni*, consists of (1R*,2R*,3S*)-(2,3,4,4-tetramethylcyclopentyl)methyl acetate. Further highly irregular terpenoid structure, and the irregular terpenoid structures of related mealybug species, suggests that these insects may have unique terpenoid biosynthetic pathways.

Jocelyn G. Millar SYNLETT 2010, No. 15, pp 2319-2321 reported synthesis of pheromones involving Ireland-Claisen conditions in seven steps (scheme 1 below) also discloses commercial development for detection, monitoring, and control of longtailed mealybugs and the leafroll viruses that they vector.

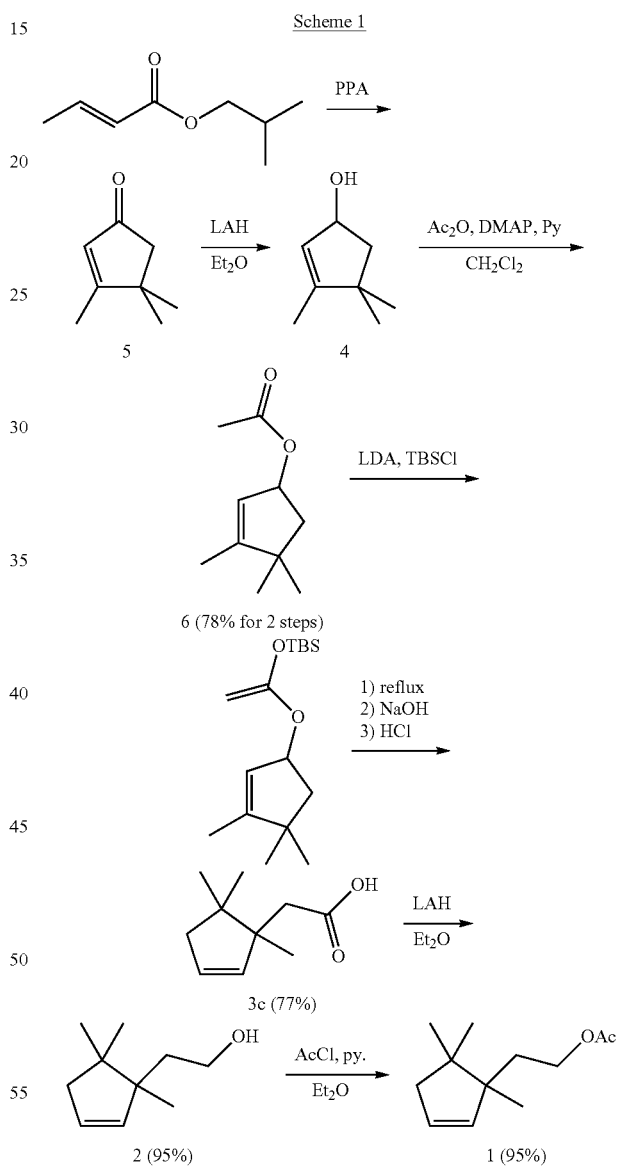

Scheme 1

Similarly, Yunfan Zou et al discloses synthesis of the Pheromone of the Longtailed Mealybug, a Sterically Congested, Irregular Monoterpenoid in J. Org. Chem. 2009, 74, 7207-7209 7207 with 13.5% overall yield wherein the key steps included regiospecific cyclization of an R-diazo-β-ketoester to build the cyclopentane ring, followed by reduction of the enol triflate of the ketone to place the double bond.

Article titled a new class of monoterpene structure by Jocelyn G. Millar et al. in Org. Lett., 2009, 11 (12), pp 2683-2685 deals with the sex pheromone of the longtailed mealybug, where 2-(1,5,5-trimethylcyclopent-2-en-1 yl)ethyl acetate was identified as a new monoterpenoid skeleton. A [2,3]-sigmatropic rearrangement was used in a key step during construction of the sterically congested tetraalkylcylopentene framework (cf below scheme 2).

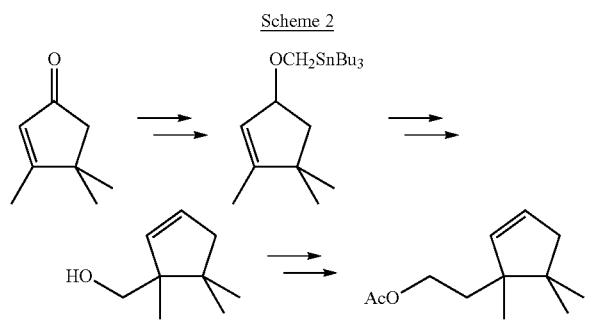

Additionally Ezra Dunkelblum has developed a practical synthesis of the *P. citri* pheromone, using two ozonolysis steps and a selective reduction of an aldehydic group in a ketoaldehyde intermediate and the same is reported in IOBC wprs Bulletin Vol. 25, 2002.

In view of prior art, pheromones are usually obtained in μg to mg quantities which are insufficient for the determination of their absolute configuration as well as for the biological studies to examine their practicality in the field. Pheromone synthesis is therefore important in order to rigorously establish the structure of a new pheromone and also to provide a plenty of material to carry out extensive biological tests.

In view of the technical constraints such as poor yield, activity, complex stereocenteres and cumbersome resolution, the present inventors have developed efficient synthesis for preparation of biologically active and commercially viable enantiomers of sex hormones in high yield.

OBJECTIVES OF THE INVENTION

The main object of the invention is to provide an enantioselective process for preparation of enantiomers of sex pheromones of the long-tailed Mealybug with high enantiopurity having significant biological activity.

SUMMARY OF THE INVENTION

Accordingly, the present invention provides an enantioselective process for preparation of biologically active (R) and (S) enantiomers of sex pheromones:

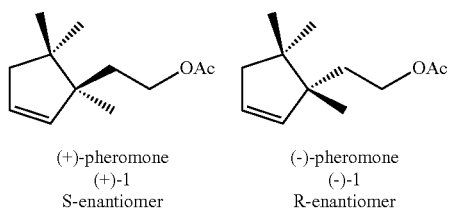

wherein, the process comprises the steps of:

a) subjecting 3,3-dimethylhex-5-en-2-one (2) to Meyer-Schuster rearrangement reaction in presence of ethoxyacetylene and an organolithium reagent, followed by treatment with Lewis acid catalyst and then reduction to obtain racemic (2E,Z)-3,4,4-trimethylhepta-2,6-dien-1-ol (3);

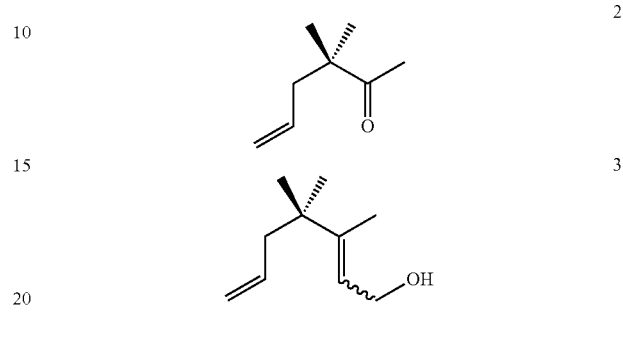

b) conducting Claisen rearrangement reaction on compound (3) in presence of alkyl vinyl ether and source of mercury ion, followed by reduction to obtain racemic 3,4,4-trimethyl-3-vinyl-hept-6-en-1-ol (4);

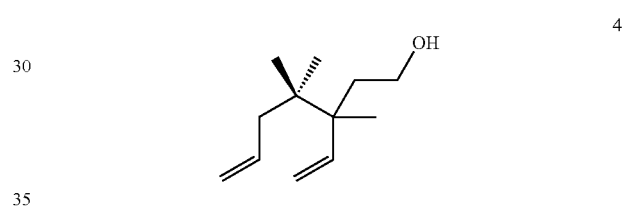

c) esterifying alcohol (4) with a chiral acid in presence of a coupling agent and base to obtain a mixture of diastereomers (5a) and (5b) followed by chiral separation;

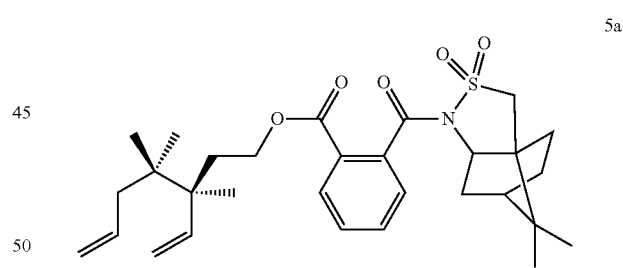

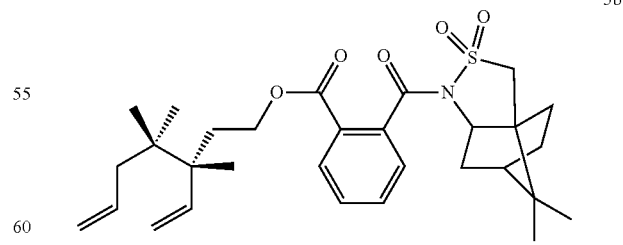

d) hydrolyzing diastereomer (5a) and (5b) separately in alkaline medium followed by acetylation in presence of acetic anhydride, acetic acid, or acetyl chloride to obtain R and S enantiomer of (3,4,4-trimethyl-3-vinyl-hept-6-enyl) acetate (6a) and (6b); and

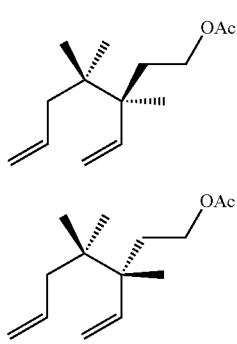

e) subjecting compound (6a) and (6b) to ring closure metathesis in presence of (Grubbs-II catalyst) [1,3-bis-(2,4,6-trimethylphenyl)-2-imidazolidinylidene]dichloro(phenylmethylene) (tricyclohexyl phosphine) ruthenium to obtain the S and R enantiomers 2-(1,5,5-trimethylcyclopent-2-en-1-yl)ethyl acetate.

In an embodiment of the present invention the organolithium reagent is selected from the group consisting of n-butyllithium, methyllithium, t-butyllithium or hexyllithium.

In another embodiment of the present invention the Lewis acid catalyst is selected from the group consisting of copper (II) triflate, indium(III)chloride, scandium(III) triflate; preferably scandium(III) triflate [Sc(OTf)$_3$].

Still in another embodiment of the present invention the alkyl group in alkyl vinyl ether is selected from the group consisting of methyl, ethyl, propyl, isopropyl, n-butyl, tert-butyl, isobutyland mercury ion source is selected from the group consisting of mercury acetate, mercury formate, mercury oxide or mixtures thereof.

Still in another embodiment of the present invention the reduction is carried out in presence of reducing agent selected from the group consisting of lithium aluminium hydride, sodium borohydride, sodium amalgam, diborane, diisobutylaluminium hydride preferably Diisobutylaluminium hydride (DIBAL-H).

Still in another embodiment of the present invention the chiral acid is selected from the group consisting of (−)-10,2-Camphorsultam; (+)-10,2-Camphorsultam; N-(2-Carboxybenzoyl)-(−)-10,2-camphorsultam; N-(2-Carboxybenzoyl)-(+)-10,2-camphorsultam or camphorsultam phthalic acid (CSP); N-(2-Carboxy-4,5-dichlorobenzoyl)-(−)-10,2-camphorsultam; N-(2-Carboxy-4,5-dichlorobenzoyl)-(+)-10,2-camphorsultam or camphorsultam dichlorophthalic acid (CSDP).

Still in another embodiment of the present invention the coupling agent is selected from the group consisting of pyridine, 4-Dimethylaminopyridine (DMAP), N,N'-Dicyclohexylcarbodiimide (DCC), Hydroxybenzotriazole (HOBT), (Benzotriazol-1-yloxy) tris(dimethylamino)phosphonium hexafluorophosphate (BOP), N,N-Diisopropyl ethylamine (DIEA), O-Benzotriazole-N,N,N',N'-tetramethyluronium-hexafluorophosphate; N,N,N',N'-tetramethyl-o-(benzotriazol-1-yl)uronium tetrafluoroborate (TBTU).

Still in another embodiment of the present invention the base is an organic base selected from the group consisting of dimethylamine, diethylamine, trimethylamine, triethylamine, tributylamine, dimethylaniline, pyridine or mixtures thereof.

Still in another embodiment of the present invention the alkaline medium is selected from the group consisting of alkali metal hydroxide, alkali metal carbonate, alkali metal bicarbonates in lower alcohol such as (C1-C6) alcohol.

Still in another embodiment of the present invention the yield of S and R enantiomers 2-(1,5,5-trimethylcyclopent-2-en-1-yl)ethyl acetate is in the range of 70-80%.

BRIEF DESCRIPTION OF ACCOMPANYING DRAWINGS

FIG. 1 depicts Male long tailed mealybugs caught in traps baited with each of the enantiomers of the pheromone, and the racemate. No mealybugs were caught in solvent treated controls.

DETAILED DESCRIPTION OF THE INVENTION

The expression '(−)-1' or '(R)-1' or '(−) pheromone' or '(R)-enantiomer' or (R)-pheromone' or '(−) 2-(1,5,5-trimethylcyclopent-2-en-1-yl)ethyl acetate' or '2-[(1R)-1,5,5-trimethylcyclopent-2-en-1-yl]ethyl acetate' are used interchangeably throughout the specification.

Similarly, the expression '(+)-1' or '(S)-1' or '(+) pheromone' or '(S)-enantiomer' or '(S)-pheromone' or '(+) 2-(1,5,5-trimethylcyclopent-2-en-1-yl)ethyl acetate' or "2-[(1S)-1,5,5-trimethylcyclopent-2-en-1-yl]ethyl acetate" are used interchangeably throughout the specification and the same may be appreciated as such by the person skilled in the art.

The invention relate to novel synthetic route for preparation of enantiomers (represented by (+) 1 and (−) 1) of sex pheromones of the long-tailed Mealybug with high enantiopurity having significant biological activity. The synthetic route provides further resolution of highly attractive sex pheromones by means of atom-economy, converting carbonyl compound into desired quaternary chiral centers.

Structures of Sex Pheromones of the Long-Tailed Mealybug

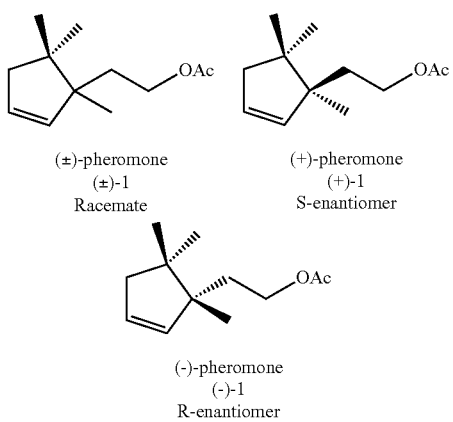

The invention particularly provides enantioselective process for preparation of (S) and (R) enantiomers (represented by (+) 1 and (−) 1) of sex pheromones of the long-tailed Mealybug with high enantiopurity comprises:

1. Converting methyl ketone (2) into allylic alcohol (3) in presence of suitable nucleophile, organolithium reagent, a suitable Lewis acid catalyst in organic solvent;

2. Rearranging compound (3) in presence of alkyl vinyl ether and source of mercury ion, followed by reduction of resulting crude aldehyde to obtain racemic compound (4);

3. Esterifying alcohol (4) with suitable chiral acid in presence of suitable coupling agent and base to obtain a mixture of diastereomers (5a) and (5b) followed by chiral separation;

4. Hydrolyzing ester of (5a) and (5b) in alkaline medium followed by acetylation to obtain compound (6a) and (6b);

5. Subjecting compound 6a and 6b to ring closure metathesis to yield the desired enantiomers (+) 1 and (−) 1.

The preparation of enantiopure pheromones is represented herein below in Scheme 3

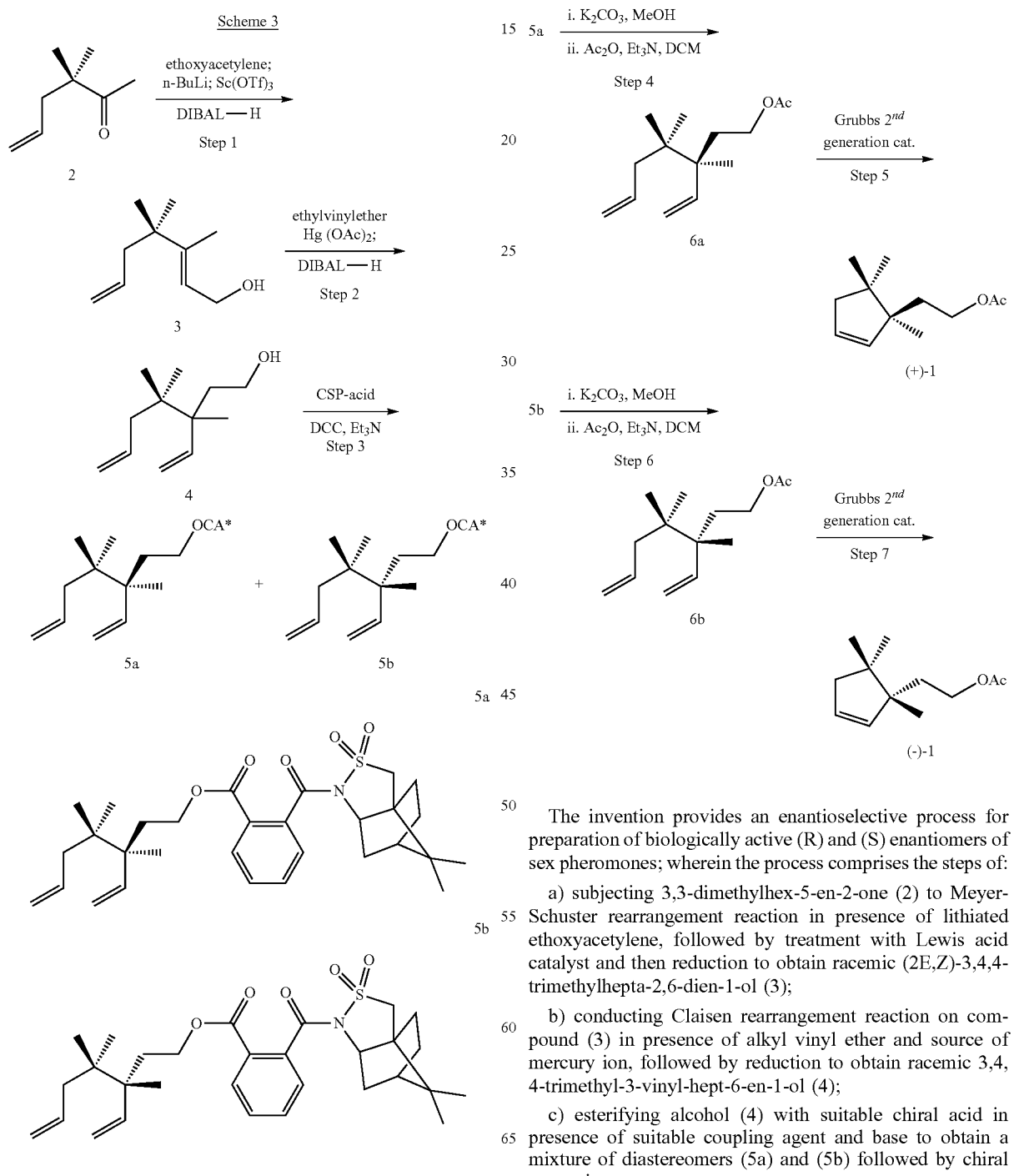

ORTEP of 5b

The invention provides an enantioselective process for preparation of biologically active (R) and (S) enantiomers of sex pheromones; wherein the process comprises the steps of:

a) subjecting 3,3-dimethylhex-5-en-2-one (2) to Meyer-Schuster rearrangement reaction in presence of lithiated ethoxyacetylene, followed by treatment with Lewis acid catalyst and then reduction to obtain racemic (2E,Z)-3,4,4-trimethylhepta-2,6-dien-1-ol (3);

b) conducting Claisen rearrangement reaction on compound (3) in presence of alkyl vinyl ether and source of mercury ion, followed by reduction to obtain racemic 3,4,4-trimethyl-3-vinyl-hept-6-en-1-ol (4);

c) esterifying alcohol (4) with suitable chiral acid in presence of suitable coupling agent and base to obtain a mixture of diastereomers (5a) and (5b) followed by chiral separation;

d) hydrolyzing diastereomer (5a) and (5b) separately in alkaline medium followed by acetylation to obtain R and S enantiomer of (3,4,4-trimethyl-3-vinyl-hept-6-enyl) acetate (6a) and (6b);

e) subjecting compound (6a) and (6b) to ring closure metathesis in presence of (Grubbs-II catalyst) to yield the S and R enantiomers of 2-(1,5,5-trimethylcyclopent-2-en-1-yl)ethyl acetate.

According to the scheme 3, the first step of the synthetic route comprises transformation of methyl ketone (2) into an allylic alcohol (3) by Meyer-Schuster rearrangement.

The reaction of ketone (2) is carried out in presence of suitable nucleophile such as ethoxyacetylene and the like in suitable organic solvent and in presence of organolithium reagent such as but not limited to n-butyllithium, methyllithium, t-butyllithium or hexyllithium.

The methyl ketone (2) is reacted with lithiated ethoxyacetylene, followed by treatment with Lewis acid catalyst selected from the group copper (II) triflate, indium(III) chloride; scandium(III) triflate or suitable catalyst thereof. In instant process extremely active, efficient, recoverable and reusable Lewis acid catalyst, such as Scandium (III) triflate $Sc(OTf)_3$ is employed to result good yield of $\alpha,\beta$-unsaturated ester, which is reduced with reducing agent selected from the group lithium aluminium hydride, sodium borohydride, sodium amalgam, diborane, diisobutylaluminium hydride and like thereof preferably Diisobutylaluminium hydride (DIBAL-H) to provide the allylic alcohol (3) in good yields, wherein yield is more than 99%. The allylic alcohol (3) i.e. E,Z-isomers are not isolated or identified as both isomers lead to single compound in next step. The organic solvent used in the first step is not limited to organic solvents such as THF, DMC, ether, hexane, diethyl ether, ethyl acetate or mixtures thereof.

Further the Claisen rearrangement in compound (3) followed by reduction of resulting crude aldehyde provided the vinyl compound (4) with desired quaternary center installation. In step 2 the rearrangement is mainly carried out in presence of alkyl vinyl ether and source of mercury ion, wherein the alkyl group in alkyl vinyl ether may be selected from the group (C1-C6) branched or linear alkyl such as methyl, ethyl, propyl, isopropyl, isobutyl, tert-butyl n-butyl like thereof. The mercury ion source is established from the group such as mercury acetate, mercury formate, mercury oxide or suitable mercury salt. Further the reduction of crude aldehyde is carried out in presence of reducing agent selected from the group consisting of lithium aluminium hydride, sodium borohydride, sodium amalgam, diborane, diisobutylaluminium hydride and like thereof preferably Diisobutylaluminium hydride (DIBAL-H).

Further in step 3, the racemic vinyl alcohol compound (4) is resolved into separate enantiomers in presence of chiral auxiliary in suitable organic solvent, where chiral auxiliary selected from camphor derivatives such as camphanol, camphanediol, camphor acid, camphorsultam or derivatives thereof or other suitable chiral acids; wherein camphorsultam derivatives may include the group consisting of substituted or unsubstituted aroyl, (C1-C8) alkanoyl, (C2-C8) alkene-oyl, heterocyclic, alicyclic compounds and like thereof, where substituents are not limited to group such as hydroxy, halide, nitro, carboxy, carbonate, (C1-C5) alkyl, aryl, arylalkyl, alkoxy, heterocyclic compounds consisting of at least one heteroatom such as oxygen, sulfur, nitrogen.

The right chiral auxiliary which can help in determining the absolute configuration through crystal structure is selected preferably from the group of camphorsultam or its derivative, such as (−)-10,2-Camphorsultam,(+)-10,2-Camphorsultam,N-(2-Carboxybenzoyl)-(−)-10,2-camphorsultam, N-(2-Carboxybenzoyl)-(+)-10,2-camphorsultam or camphorsultam phthalic acid (CSP); N-(2-Carboxy-4,5-dichlorobenzoyl)-(−)-10,2-camphorsultam, N-(2-Carboxy-4,5-dichlorobenzoyl)-(+)-10,2-camphorsultam or camphorsultam dichlorophthalic acid (CSDP).

According to step 3, alcohol (4) is esterified with chiral acid in presence of suitable coupling agent and base to produce a mixture of diastereomers 5a and 5b; wherein the suitable coupling agent is selected from N,N'-Dicyclohexylcarbodiimide (DCC), Hydroxybenzotriazole (HOBT), (Benzotriazol-1-yloxy) tris(dimethylamino)phosphonium hexafluorophosphate (BOP), N,N-Diisopropyl ethylamine (DIEA), O-Benzotriazole-N,N,N',N'-tetramethyl-uronium-hexafluorophosphate; N,N,N',N'-tetramethyl-o-(benzotriazol-1-yl)uronium tetrafluoroborate (TBTU) or any suitable coupling agent known in the art.

Further the mixtures of diastereomers (5a) and (5b) are separated by chiral chromatography such as TLC, HPLC or equivalent techniques. The relative and absolute configuration of 5a and 5b is determined through X-ray crystal structure analysis.

According to the invention the enantiomer compound (5a) and (5b) can be further converted into desired sex pheromones (+) 1 and (−) 1 with absolute configuration via formation of intermediate compound (6a) and (6b) respectively.

With regard to step 4 and 6, the camphorsultam ester (5a) and (5b) is hydrolyzed at ambient temperature with the aid of hydrolyzing agent such as alkali metal hydroxide, alkali metal carbonate, alkali metal bicarbonates in lower alcohol such as (C1-C6) alcohol, followed by acetylation produced the compound (6a) and (6b).

The acetylation reaction may be carried out in presence of acetic anhydride, acetic acid, acetyl chloride in suitable base.

Further the base employed in the instant process steps is an organic base, selected from the group consisting of dimethylamine, diethylamine, trimethylamine, triethylamine, tributylamine, dimethylaniline, pyridine or mixtures thereof, preferably base is. triethylamine.

Consequently, as depicted in scheme 3, where (6a) intermediate compound is subjected to ring closure metathesis to afford the desired (S)-enantiomer of sex pheromones i.e (+)-1 in high yield and purity, similarly 6b compounds generated (R) enantiomer of sex pheromones i.e. (+)-1.

The ring closure metathesis is preferably carried out in presence of (Grubbs-II catalyst) i.e. [1,3-bis-(2,4,6-trimethylphenyl)-2-imidazolidinylidene]dichloro(phenylmethylene) (tricyclohexyl phosphine) ruthenium.

Additionally the purification of crude product in any step is carried out by the known technique in suitable organic solvents such as ethyl acetate, hexanes, ether, lower alcohol, DMC, THF, DMSO, water, Toluene, chloroform either alone or in mixtures thereof.

The enantiomers obtained from the instant synthetic route are highly pure with excellent yield which is more than 80%.

The invention provides an enantiopure sex pheromone of 2-(1,5,5-trimethylcyclopent-2-en-1-yl)ethyl acetate comprising R and S enantiomers; and characterized by known techniques.

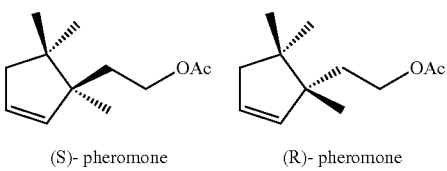

(S)- pheromone     (R)- pheromone

Further the biological activities of each enantiomer and racemate, of pheromone are evaluated, where (S)-(+)-enantiomer is found to be highly attractive to male mealybugs (cf FIG. 1), implies that female longtailed mealybugs produce (S) enantiomer. The (R)-(−)-enantiomer is only slightly more attractive than solvent-treated controls due to the contamination of (R) enantiomer with 1.7% of the bioactive (S)-enantiomer.

Furthermore, the racemate (±1) is as attractive as the pure enantiomer, indicating that the (R)-(−)-enantiomer is not inhibitory.

The enantiomers of the present invention are characterized by spectral analysis such as NMR, IR, Mass and UV, elemental analysis and melting point etc.

Following are the examples given to further illustrate the invention and should not be construed to limit the scope of the present invention.

EXAMPLES

All reactions were carried out in oven-dried glassware under argon or nitrogen unless otherwise specified, with magnetic stirring. Air sensitive reagents and solutions were transferred via syringe or cannula and were introduced to the apparatus via rubber septa. All reagents, starting materials, and solvents were obtained from commercial suppliers and used without further purification. Reactions were monitored by thin layer chromatography (TLC) with 0.25 mm pre-coated silica gel plates (60 F254). Visualization was accomplished with either UV light, iodine vapors, or by immersion in ethanolic solutions of phosphomolybdic acid, para-anisaldehyde, or KMnO4 followed by heating with a heat gun for ~15 s. Flash column chromatography was performed on silica gel (100-200 or 230-400 mesh size). High resolution mass spectra (HRMS, ESI) were recorded with an ORBITRAP mass analyzer (Q Exactive). Mass spectra were measured with electrospray ionization with an MSQ LCMS mass spectrometer. Infrared (IR) spectra were recorded on a FT-IR spectrometer as thin films. Optical rotations were recorded on a polarimeter at 589 nm.

Example 1

Preparation of (2E, Z)-3,4,4-trimethylhepta-2,6-dien-1-ol (3)

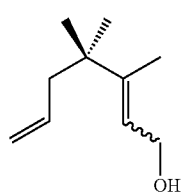

To a THF solution (60 mL) of ethoxyacetylene (12 mL, 50% in hexane, 95.2 mmol) was added n-BuLi (22 mL, 35.7 mmol, 1.6M in hexane) drop wise over 15 min. at −78° C. under argon atmosphere. The reaction mixture was allowed to warm at 0° C. over 1 h and held at 0° C. for an additional 45 min. The solution was recooled to −78° C. and 3,3-dimethylhex-5-en-2-one 2 (3 g, 23.8 mmol) was added in one portion. The reaction mixture was allowed to warm to rt over 1 h and held at rt (25° C.) for an additional 4 h. Saturated aq. $NH_4Cl$ (25 mL) was added to quench the reaction and reaction mixture was extracted with diethyl ether (30 mL×3), combined organic layer washed with brine (30 mL) and dried over anhydrous $Na_2SO_4$. The solvent was removed in vacuo to furnish 1-ethoxy-3,4,4-trimethyl-hept-6-en-1-yn-3-ol (4.3 g); which was used crude as such for next step without further purification.

To a 4:1 v/v $CH_2Cl_2$/ethanol solution (30 mL) of 1-ethoxy-3,4,4-trimethyl-hept-6-en-1-yn-3-ol (4.3 g, 21.9 mmol) in an open flask was added Sc (OTf)$_3$ (117 mg, 0.238 mmol). Reaction mixture was stirred at rt (25° C.) for another 6 h. Excess of solvent removed in vacuo and crude product obtained was purified by silica gel column chromatography with 2% EtOAc/hexanes to furnish ethyl (2E,Z)-3,4,4-trimethylhepta-2,6-dienoate (3.35 g, 71% over two steps) as a mixture of cis and trans isomers. Rf=0.70 (20% EtOAc/hexanes; $^1$H NMR (400 MHz, CDCl$_3$) Assignment for mixture cis and trans isomer (1:1 ratio); δ 1.08 (s, 6H), 1.16 (s, 6H), 1.28 (t, J=7.2 Hz, 6H), 1.82 (s, 3H), 2.15 (s, 3H), 2.17 (d, J=7.2 Hz, 2H), 2.38 (d, J=7.2 Hz, 2H), 4.10-4.16 (m, 4H), 4.97-5.02 (m, 4H), 5.54-5.62 (m, 1H), 5.66 (d, J=8.8 Hz, 2H), 5.72-5.78 (m, 1H); $^{13}$C NMR (100 MHz, CDCl$_3$) δ 167.8, 167.4, 165.6, 157.7, 135.6, 134.7, 117.7, 117.3, 117.0, 114.6, 60.2, 59.6, 45.6, 45.0, 41.1, 39.7, 27.1 (2C), 26.5 (2C), 24.7, 15.2, 14.7, 14.3; LCMS (ES) [M+1]+ m/z 197.2; HRMS (ESI): m/z calculated for $C_{12}H_{21}O_2$ [M+H]+ 197.1541. found 197.1535; IR (thin film) 2976, 1717, 1636, 1445, 178, 1045, 913 cm-1.

To a solution of ethyl (2E,Z)-3,4,4-trimethylhepta-2,6-dienoate (2.0 g, 1.02 mmol) in $CH_2Cl_2$ (50 mL), DIBAL-H (Diisobutylaluminium hydride) (25 mL, 2.04 mmol, 1M in THF) was added at −20° C. during 15 min and stirred at same temperature for another 1 h and an additional 1 h at 0° C. Reaction mixture was diluted with saturated $NH_4Cl$ (25 mL) and DCM was added (100 mL). Reaction mixture was taken in separating funnel and organic layer washed with 1N HCl (50 mL×3) and layers were separated, organic layer further washed with water (100 mL) and brine (50 mL), dried over anhydrous $Na_2SO_4$ and concentrated in vacuo followed by purification by column chromatography to furnish (2E,Z)-3,4,4-trimethylhepta-2,6-dien-1-ol (3) (1.56 g, 99%). Rf=0.35 (20% EtOAc/hexanes); $^1$H NMR (400 MHz, CDCl$_3$) Assignment for major isomer δ 1.03 (s, 6H), 1.64 (s, 3H), 2.11 (d, J=7.2 Hz, 2H), 4.20 (d, J=6.4 Hz, 2H), 4.95-5.01 (m, 2H), 5.38-5.43 (m, 1H), 5.57-5.68 (m, 1H); $^{13}$C NMR (100 MHz, CDCl3) δ 145.0, 135.7, 122.5, 116.5, 60.0, 45.1, 39.2, 26.8 (2C), 12.8; LCMS (ES) [M+NH4]+ m/z 170.9.

Example 2

3,4,4-trimethyl-3-vinyl-hept-6-en-1-ol (4)

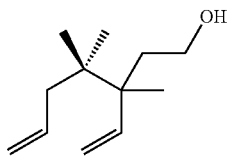

4

To a flame-dried Schlenk tube was added (2E,Z)-3,4,4-trimethylhepta-2,6-dien-1-ol (3) (1.6 g, 10.38 mmol), ethyl vinyl ether (50 mL), and then Hg(OAc)$_2$ (970 mg, 3.05 mmol, 0.28 equiv). The reaction mixture was sealed and stirred at 45° C. for 96 h. After cooling to rt (25° C.), K$_2$CO$_3$ (7.2 g, 51.9 mmol, 5.4 equiv) added, and the suspension was stirred for 30 min. Then, the mixture was filtered, and the solution was concentrated under reduced pressure. Purification by column chromatography (10:1 hexane-EtOAc as eluent) afforded 3,4,4-trimethyl-3-vinyl-hept-6-en-1-ol (850 mg, 76%) and used for next step without characterization and starting allylic alcohol (650 mg).

To a above solution of 3,4,4-trimethyl-3-vinyl-hept-6-en-1-ol (850 mg, 4.72 mmol) in CH$_2$Cl$_2$ (20 mL) was added drop wise DIBAL-H (1 M in toluene, 8.6 mL, 0.60 mmol) at −40° C. The reaction mixture was allowed to warm to rt (25° C.) and stirred for 2 h, after which it was quenched with excess of saturated Na$_2$SO$_4$ (3 mL). After 30 min stirring, the cloudy suspension was filtered, and the solution was concentrated under reduced pressure. Purification by column chromatography (2:9 EtOAc-hexane as eluent) afforded the 3,4,4-trimethyl-3-vinyl-hept-6-en-1-ol (4) (740 mg, 87%); Rf=0.25 (15% EtOAc:hexanes); $^1$H NMR (400 MHz, CDCl$_3$) δ 0.82 (s, 6H), 0.97 (s, 3H), 1.64-1.71 (m, 1H), 1.77-1.84 (m, 1H), 2.01 (d, 7.2 Hz, 2H), 3.59 (t, J=7.2 Hz, 2H), 4.93-5.03 (m, 3H), 5.11 (dd, J=10.8, 1.6 Hz, 1H), 5.75-5.86 (m, 1H), 5.91 (dd, J=17.6, 11.2 Hz, 1H); $^{13}$C NMR (100 MHz, CDCl$_3$) δ 144.2, 136.5, 117.0, 114.0, 60.7, 44.4, 41.6, 38.6, 37.5, 21.8 (2C), 16.7; LCMS (ES) [M+1]+ m/z 183.2; HRMS (ESI): m/z calculated for C$_{12}$H$_{23}$O [M+H]+ 183.1748. found 183.1741; IR (neat) 3325, 2966, 1828, 1637, 1414, 1373, 1049, 1010, 911, 799 cm-1.

Example 3

(3,4,4-trimethyl-3-vinyl-hept-6-enyl) acetate (6)

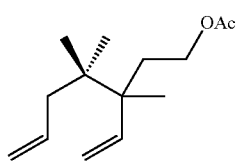

6

A solution of 3,4,4-trimethyl-3-vinyl-hept-6-en-1-ol (4) (100 mg, 0.54 mmol) and Et$_3$N (0.30 mL, 2.19 mmol) in dry CH$_2$Cl$_2$ (5 mL) was treated with acetic anhydride (0.10 mL, 1.09 mmol) and catalytic amount of DMAP (3 mg) at rt (exact temp??). After being stirred at for 4 h, reaction mixture was diluted with water (10 mL) and extracted with DCM (10 mL×3) combined organic layer was washed with brine (10 mL) and dried over Na$_2$SO$_4$. Solvent was removed under reduced pressure and purification on column chromatography furnished the compound (6) (112 mg, 90%). Rf=0.75 (20% EtOAc:hexanes); $^1$H NMR (400 MHz, CDCl$_3$) δ 0.82 (s, 6H), 0.98 (s, 3H), 1.69-1.84 (m, 2H), 2.01-2.05 (m, 5H), 3.93-4.05 (m, 2H), 4.92-5.03 (m, 3H), 5.13 (dd, J=11.0, 1.3 Hz, 1H), 5.75-5.85 (m, 2H); $^{13}$C NMR (100 MHz, CDCl$_3$) δ 171.3, 142.9, 136.4, 117.2, 114.6, 62.9, 44.2, 41.5, 38.7, 32.9, 21.7 (2C), 21.2, 16.7; IR (thin film) 2253, 1732, 1542, 1472, 1377 cm-1.

Example 4

2-(1,5,5-trimethylcyclopent-2-en-1-yl) ethyl acetate (Racemic 1)

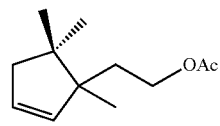

1

Racemic

To a above solution of 6 (82 mg, 0.36 mmol) in dry CH2Cl2 (5 mL) was degassed for 10 min. in a stream of argon and then treated with Grubbs' 2nd generation catalyst (31 mg, 10 mol %) in one portion. After being heated at 40° C. for 16 h, it was treated with a drop of DMSO and stirring was continued for an hour. Evaporation of the solvent and purification by column chromatography (5% EtOAc-hexanes as eluent) furnished the (2-(1,5,5-trimethylcyclopent-2-en-1-yl)ethyl acetate (1) (52 mg, 72%). $^1$H NMR (400 MHz, CDCl3) δ 0.89 (s, 3H), 0.94 (s, 3H), 0.95 (s, 3H), 1.52-1.58 (m, actual ddd merged in CDCl$_3$ moisture, 1H), 1.80 (ddd, J=13.2, 9.6, 6.0 Hz, 1H), 2.04 (s, 3H), 2.12 (t, J=1.6 Hz, 2H), 4.09 (ddd, J=16.0, 9.6, 6.0H, 1H), 4.19 (ddd, J=16.4, 10.8, 6.0 Hz, 1H), 5.54 (dt, J=5.6, 2.4 Hz, 1H), 5.62 (dt, J=5.6, 2.4 Hz, 1H); 13C NMR (100 MHz, CDCl$_3$, residual peak at 77.160) δ 171.2, 138.9, 128.3, 62.8, 49.6, 47.0, 44.2, 34.8, 24.8, 24.2, 21.1, 19.5; LCMS (ES) [M+H]+ m/z 197.1; IR (thin film CHCl3) 3050, 2962, 1742, 1459, 1365, 1235, 1052, 1030 cm-1.

Example 5

Preparation of CSP-ester (5a and 5b)

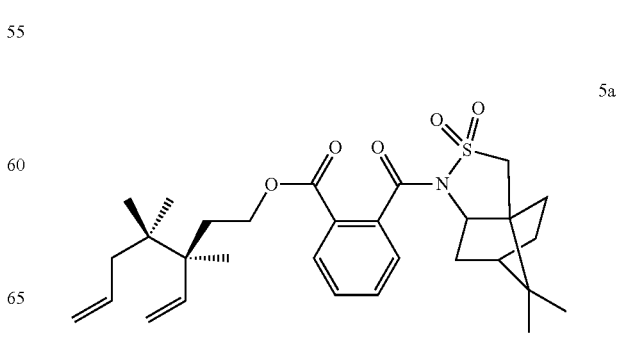

5a

-continued

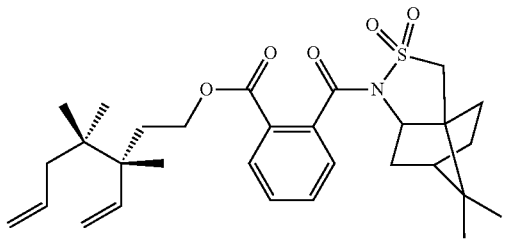

5b

A solution of 3,4,4-trimethyl-3-vinylhept-6-en-1-ol 4 (50 mg, 0.27 mmol) and N-(2-carboxybenzoyl)-(−)-10,2-camphorsultam (131 mg, 0.36 mmol) in $CH_2Cl_2$ (5 mL) was treated with dimethylaminopyridine (DMAP, 44 mg, 0.36 mmol) followed by dicyclohexylcarbodiimide (DCC, 61 mg, 0.30 mmol) at 0° C. After stirring at rt (25° C.) for 24 h, the reaction mixture was filtered, and the filtrate was concentrated under reduced pressure. The residue was purified by flash chromatography yielding the mixture of diastereomers (105 mg, 74%). Rf=0.2 (20% EtOAc:hexanes).

The mixtures of diastereomers were separated by preparative HPLC using following conditions:
Prep System: Prep-K 100, YMC make
Prep Column: CHIRALPAK AD-H (30×250) mm, Daicel make
Chromatogram Conditions:
Sample analysis Column ID: CHIRALPAK IA-3 (4.6×250 mm), 3μ
Mobile phase: n-Hexane:EtOH (95/05)
Flow: 1.0 mL/min, Temp: 25° C.
UV: 224 nm.
Analytical Data for Separated Diastereomers:

a) Diastereomer-I: (5a) (S)-3,4,4-trimethyl-3-vinyl-hept-6-en-1-yl 2-((3aR,6R)-8,8-dimethyl-2,2-dioxidohexahydro-3H-3a,6-methanobenzo[c]isothiazole-1-carbonyl)

$[\alpha]_{22}D$−122.6 (c 0.5, CH2Cl2); 1H NMR (400 MHz, CDCl3) δ 0.83 (s, 6H), 0.97 (s, 3H), 1.01 (m, 3H), 1.23 (s, 3H), 1.25-1.47 (m, 3H), 1.82-1.98 (m, 5H), 2.02 (d, J=6.8 Hz, 1H), 2.10-2.19 (m, 1H), 2.42-2.50 (br s, 1H), 3.40 (ABq, J=14 Hz, 2H), 4.06-4.10 (m, 1H), 4.20 (t, J=7.6 Hz, 2H), 4.93-5.03 (m, 3H), 5.13 (dd, J=10.8, 1.2 Hz, 1H), 5.76-5.87 (m, 2H), 7.45 (d, J=7.6 Hz, 1H), 7.52 (dt, J=7.6, 1.2 Hz, 1H), 7.57 (dt, J=7.6, 1.2 Hz, 1H), 7.99 (d, J=8 Hz, 1H); 13C NMR (100 MHz, CDCl3): δ 167.9, 165.3, 143.0, 136.3, 135.8, 131.9, 130.3, 129.7, 129.5, 129.1, 117.1, 114.6, 65.9, 63.8, 53.2, 48.5, 47.9, 45.0, 44.4, 41.6, 38.7, 37.9, 33.3, 32.9, 26.6, 21.8 (2C), 20.9, 20.2, 16.8; HRMS (ESI): m/z calculated for C30H42NO5S [M+H]+ 528.2778. found 528.2787; Chiral HPLC purity (%)=98.2; TR: 10.57, Column ID: CHIRALPAK IA-3 (4.6×250 mm), 3μ, Mobile Phase: n-Hexane:EtOH (95/05), Flow: 1.0 mL/min, Temp: 25° C., UV at 224 nm; IR (Thin film CHCl3) 2963, 1721, 1686, 1635, 1336, 1300, 1168, 1112, 1083, 912, 776 cm-1.

b) Diastereomer-II: (5b) ((R)-3,4,4-trimethyl-3-vinylhept-6-en-1-yl 2-((3aR,6R)-8,8-dimethyl-2,2-dioxidohexahydro-3H-3a,6-methanobenzo[c]isothiazole-1-carbonyl)benzoate $[\alpha]_{21}D$−68.2 (c 0.5, $CH_2Cl_2$); 1H NMR (400 MHz, CDCl3) δ 0.83 (s, 6H), 0.97 (s, 3H), 1.00 (m, 3H), 1.23 (s, 3H), 1.25-1.47 (m, 3H), 1.80-1.97 (m, 5H), 2.03 (d, J=7.6 Hz, 1H), 2.10-2.19 (m, 1H), 2.42-2.50 (m, 1H), 3.40 (ABq, J=14 Hz, 2H), 4.06-4.10 (m, 1H), 4.13-4.27 (m, 2H), 4.95-5.03 (m, 3H), 5.14 (d, J=11.2 Hz, 1H), 5.76-5.89 (m, 2H), 7.45 (d, J=6.8 Hz, 1H), 7.52 (app. t, J=8, 3.8 Hz, 1H), 7.58 (app. t, J=7.2, 14.8 Hz, 1H), 7.99 (d, J=8 Hz, 1H); 13C NMR (100 MHz, CDCl3): δ 167.9, 165.3, 143.0, 136.3, 135.8, 131.8, 130.3, 129.7, 129.5, 129.1, 117.1, 114.5, 65.9, 63.8, 53.2, 48.5, 47.9, 45.0, 44.4, 41.6, 38.7, 37.9, 33.3, 32.9, 26.6, 21.8 (2C), 20.9, 20.2, 16.8; HRMS (ESI): m/z calculated for C30H42NO5S [M+H]+ 528.2778. found 528.2787; Chiral HPLC purity (%)=99.2; TR: 13.63, Column ID: CHIRALPAK IA-3 (4.6×250 mm), 3μ, Mobile Phase: n-Hexane:EtOH (95/05), Flow: 1.0 mL/min, Temp: 25° C., UV at 224 nm; IR (Thin film CHCl3) 2963, 1720, 1685, 1635, 1333, 1299, 1168, 1137, 1082 cm-1.

Example 6

(S) (3,4,4-trimethyl-3-vinyl-hept-6-enyl) acetate (6a)

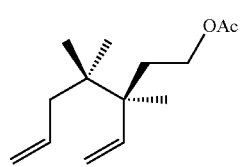

6a $K_2CO_3$ (282 mg, 2.04 mmol, 12 equiv.) was added to a solution of CSP-ester 5a (90 mg, 0.170 mmol) in methanol (3 mL) at rt (25° C.). After being stirred for another 2 h, reaction mixture was concentrated under reduced pressure and directly purification by column chromatography furnished the mixture of pure (+) 3,4,4-trimethyl-3-vinyl-hept-6-en-1-ol (28 mg, 90%). Rf=0.4 (20% EtOAc:hexanes); $[\alpha]_{25}D$+1.7 (c 0.38, $CH_2Cl_2$). The 1H NMR was compared with previously prepared compound and found to be identical.

(6a) was prepared from (+) 3,4,4-trimethyl-3-vinyl-hept-6-en-1-ol using analogues procedure described above for the preparation of racemic 6

Yield: (28 mg, 95%). Rf=0.75 (20% EtOAc:hexanes); $[\alpha]_{23}D$−4.6 (c 0.1, $CH_2Cl_2$). The 1H NMR was compared with previously prepared compound and found to be identical.

Example 7

(+) 2-(1,5,5-trimethylcyclopent-2-en-1-yl)ethyl acetate (S)-1

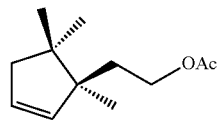

(S)-1

(+)-(1) was prepared from 6a using analogues procedure described above for the preparation of racemic 1.

Yield: (14.2 mg, 75%). Rf=0.41 (20% EtOAc:hexanes); $[\alpha]_{25}D+27.8$ (c 0.16, $CH_2Cl_2$). The $^1H$ NMR was compared with previously prepared compound and found to be identical.

Example 8

(R) (3,4,4-trimethyl-3-vinyl-hept-6-enyl) acetate (6b)

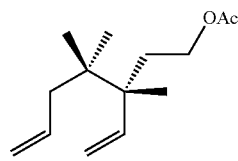

6b

Analytical data for (R) 3,4,4-trimethyl-3-vinyl-hept-6-en-1-ol:

Yield: 94%; Rf=0.4 (20% EtOAc:hexanes); $[\alpha]_{25}D-2.0$ (c 0.15, CH2Cl2). The $^1H$ NMR was compared with previously prepared compound and found to be identical.

Analytical data for (6b):

Yield: 94%; Rf=0.75 (20% EtOAc:hexanes); $[\alpha]_{25}D+3.3$ (c 0.15, $CH_2Cl_2$). The $^1H$ NMR was compared with previously prepared compound and found to be identical.

Example 9

(−) 2-(1,5,5-trimethylcyclopent-2-en-1-yl)ethyl acetate (R)-1

(R)-1

Analytical data for (−) 1/(R)-1:

Yield: 83%; Rf=0.41 (20% EtOAc:hexanes), $[\alpha]_{25}D-24.0$ (c 0.13, CH2Cl2). The $^1H$ NMR was compared with previously prepared compound and found to be identical.

Experimental a) X-Ray Crystal Structure Details

Single crystals of compound 5b were obtained from petroleum ether. X-ray intensity data were collected on a Bruker SMART APEX II CCD diffractometer with graphite-monochromatized (Mo Kα=0.71073 Å) radiation at low temperature, 150(2) K. The X-ray generator was operated at 50 kV and 30 mA. Diffraction data were collected with a ω scan width of 0.5° and at different settings of φ and 2θ. The sample-to-detector distance was fixed at 5.00 cm. The X-ray data acquisition was monitored by the APEX2 program suite. All the data were corrected for Lorentzpolarization and absorption effects using SAINT and SADABS programs integrated in the APEX2 program package. The structures were solved by the direct method and refined by full matrix leastsquares, on the basis of F2, using SHELX-97. Molecular diagrams were generated using XSHELL program integrated in SHELXTL package.11 All the H-atoms were placed in geometrically idealized position (C—H=0.95 Å for phenyl H-atoms, C—H=0.99 Å for methylene H-atoms, C—H=1.00 Å for methine H-atoms, and C—H=0.98 Å for methyl H-atoms) and constrained to ride on their parent atoms [Uiso(H)=1.2 Ueq(C) for the phenyl, methylene, and methane group, and Uiso(H)=1.5 Ueq(C) for the methyl group]. Crystallographic data for 5b (C30H41NO5S): M=527.70, Crystal dimensions 0.40×0.22×0.02 mm3, monoclinic, space group P21, a=9.8209(13), b=11.2394(16), c=13.1369(18) Å, β=107.284(10)°, V=1384.6(3) Å3, Z=2, ρ calcd=1.266 gcm-3, µ(Mo Kα)=0.157 mm-1, F(000)=568, 2θmax=50.00°, T=150(2) K, 8872 reflections collected, 4482 unique, 3055 observed (I>2σ(I)) reflections, 340 refined parameters, R value 0.0524, wR2=0.0902, (all data R=0.0954, wR2=0.1053), S=0.996, minimum and maximum transmission 0.940 and 0.997; maximum and minimum residual electron densities +0.26 and −0.23 e Å-3. The absolute configuration was established by anomalous dispersion effect (Flack parameter of 0.07(11)) in X-ray diffraction measurements, caused by the presence of the sulfur atom in the molecule.

b) Field Trial of the Pheromone Enantiomers and the Racemate (The field trials on vineyards were conducted with the help of Prof. Jocelyn Millar, University of California, Riverside, USA)

A field bioassay of the pheromone was conducted at a nursery in Bonsall, Calif., USA, in a 0.49 ha plot of Ruscus hypoglossum L. (plot coordinates: 33°17'18.36" N, 117°16'55.61" W elev 113 m) that was known to be infested with P. longispinus. The plot was divided into seven hoop houses (63 m long×7 m wide), six of which were used in this study. Each house (block) was covered in plastic with open ends. Airflow between houses was not restricted because the plastic cover began 1 m above the plant canopy. Four delta sticky traps were spaced every 12.5 m along a transect within each house, suspended directly above the ruscus canopy. Each trap contained an 11 mm gray rubber septum impregnated with a hexane solution of one of four treatments: solvent control, 5 µg of (S)-(+)-enantiomer, 5 µg of (R)-(−)-enantiomer, 10 µg of the racemate. Treatments were assigned randomly along each transect. Traps were replaced, and treatments were repositioned once after 6 d. Traps remained in place for another 11 d. Trap count data were analyzed by analysis of variance after √(x+0.5) transformation of the data to meet the assumptions of normality and equal variances. Differences among means were tested using Tukey's honestly significant differences (HSD) test. There was no significant interaction between the two sampling periods (date) and the treatments (F=3.23, df=2, 30, and P=0.054). Thus, data for each date were combined for the final analysis. There was both a significant effect of date (F=10.19, df=2, 32, P=0.0032) and treatment (F=130.04, df=2, 32, P<0.0001). Controls were not included in the analysis because their zero values and lack of variance violate the assumptions of ANOVA. Instead, confidence intervals were constructed, showing that the low trap counts for the (R)-(−)-enantiomer were significantly different than zero, i.e. that the (−)-enantiomer was slightly more attractive than controls.

ADVANTAGES OF THE INVENTION

The practically prepared enantiomers of sex pheromones are widely useful in the field of agriculture to improve the quantitative and qualitative production. In particular, enantiomer of the sex pheromone (+)1 and racemate (±)1 is economically significant due to following reasons:

1. Remarkable biological activity: In field trials, the racemic pheromone was reported to be highly attractive to male mealybugs for more than three months at 25 µg concentrations,
2. Access to optically pure pheromone: one of the enantiomer (+)1 (probably, the natural one) showed more activity than racemic pheromone,
3. Use in crop protection: may help in protecting high value crops such as grapes, citrus, apples, pears, and ornamental plants.

I claim:

1. An enantioselective process for preparation of biologically active (R) and (S) enantiomers of sex pheromones:

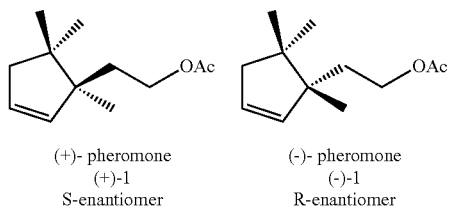

(+)- pheromone
(+)-1
S-enantiomer (-)- pheromone
(-)-1
R-enantiomer wherein, the process comprises the steps of:
a) subjecting 3,3-dimethylhex-5-en-2-one (2) to Meyer-Schuster rearrangement reaction in presence of ethoxyacetylene and an organolithium reagent, followed by treatment with Lewis acid catalyst and then reduction to obtain racemic 3,4,4-trimethylhepta-2,6-dien-1-ol (3);

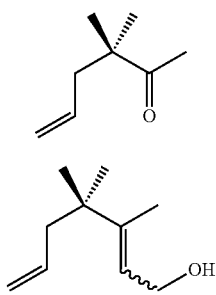

b) conducting Claisen rearrangement reaction on compound (3) in presence of alkyl vinyl ether and source of mercury ion, followed by reduction to obtain racemic 3,4,4-trimethyl-3-vinyl-hept-6-en-1-ol (4);

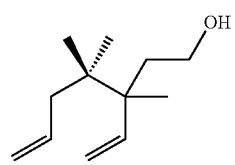

c) esterifying alcohol (4) with a chiral acid in presence of a coupling agent and base to obtain a mixture of diastereomers (5a) and (5b) followed by chiral separation;

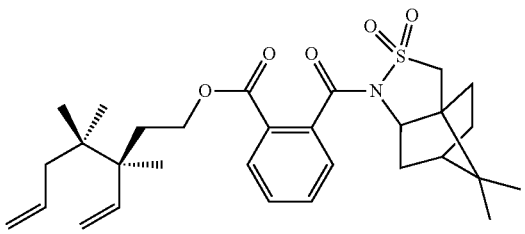

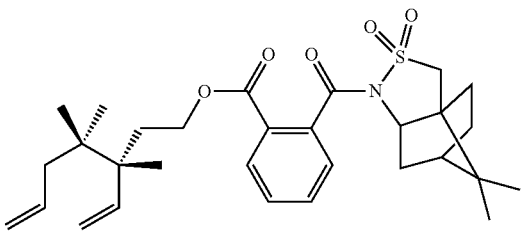

d) hydrolyzing diastereomer (5a) and (5b) separately in alkaline medium followed by acetylation in presence of acetic anhydride, acetic acid, or acetyl chloride to obtain R and S enantiomer of (3,4,4-trimethyl-3-vinyl-hept-6-enyl) acetate (6a) and (6b); and

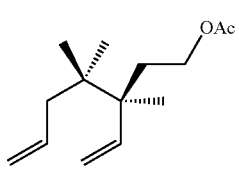

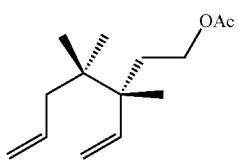

e) subjecting compound (6a) and (6b) to ring closure metathesis in presence of (Grubbs-II catalyst) [1,3-bis-(2,4,6-trimethylphenyl)-2-imidazolidinylidene]dichloro(phenylmethylene) (tricyclohexyl phosphine) ruthenium to obtain the S and R enantiomers 2-(1,5,5-trimethylcyclopent-2-en-1-yl)ethyl acetate.

2. The process as claimed in claim 1, wherein the organolithium reagent is selected from the group consisting of n-butyllithium, methyllithium, t-butyllithium, and hexyllithium.

3. The process as claimed in claim 1, wherein the Lewis acid catalyst is selected from the group consisting of copper (II) triflate, indium(III)chloride, and scandium(III) triflate.

4. The process as claimed in claim 1, wherein the alkyl group in alkyl vinyl ether is selected from the group consisting of methyl, ethyl, propyl, isopropyl, n-butyl, tert-butyl, isobutyl and mercury ion source is selected from the group consisting of mercury acetate, mercury formate, mercury oxide or mixtures thereof.

5. The process as claimed in claim 1, wherein the reduction is carried out in presence of reducing agent selected from the group consisting of lithium aluminium hydride, sodium borohydride, sodium amalgam, diborane, and diisobutylaluminium hydride.

6. The process as claimed in claim 1, wherein the chiral acid is selected from the group consisting of (−)-10,2-Camphorsultam; (+)-10,2-Camphorsultam; N-(2-Carboxybenzoyl)-(−)-10,2-camphorsultam; N-(2-Carboxybenzoyl)-(+)-10,2-camphorsultam or camphorsultam phthalic acid (CSP); N-(2-Carboxy-4,5-dichlorobenzoyl)-(−)-10,2-camphorsultam; N-(2-Carboxy-4,5-dichlorobenzoyl)-(+)-10,2-camphorsultam or camphorsultam dichlorophthalic acid (CSDP).

7. The process as claimed in claim 1, wherein the coupling agent is selected from the group consisting of pyridine, 4-Dimethylaminopyridine (DMAP), N,N'-Dicyclohexylcarbodiimide (DCC), Hydroxybenzotriazole (HOBT), (Benzotriazol-1-yloxy) tris(dimethylamino)phosphonium hexafluorophosphate (BOP), N,N-Diisopropyl ethylamine (DIEA), O-Benzotriazole-N,N,N',N'-tetramethyl-uronium-hexafluoro-phosphate, and N,N,N',N'-tetramethyl-o-(benzotriazol-1-yl)uronium tetrafluoroborate (TBTU).

8. The process as claimed in claim 1, wherein the base is an organic base selected from the group consisting of dimethylamine, diethylamine, trimethylamine, triethylamine, tributylamine, dimethylaniline, pyridine or mixtures thereof.

9. The process as claimed in claim 1, wherein the alkaline medium is selected from the group consisting of alkali metal hydroxide, alkali metal carbonate, alkali metal bicarbonates in lower alcohol such as (C1-C6) alcohol.

10. The process as claimed in claim 1, wherein the yield of S and R enantiomers 2-(1,5,5-trimethylcyclopent-2-en-1-yl)ethyl acetate is in the range of 70-80%.

11. The process as claimed in claim 3, wherein the Lewis acid catalyst is scandium(III) triflate [$Sc(OTf)_3$].

12. The process as claimed in claim 5, wherein the reduction is carried out in presence of Diisobutylaluminium hydride (DIBAL-H).

* * * * *